(12) United States Patent
Huang et al.

(10) Patent No.: US 9,648,870 B2
(45) Date of Patent: May 16, 2017

(54) ANTIMICROBIAL COMPOSITE MATERIAL AND METHOD FOR FABRICATING THE SAME

(71) Applicant: INDUSTRIAL TECHNOLOGY RESEARCH INSTITUTE, Chutung, Hsinchu (TW)

(72) Inventors: Hsin-Yi Huang, Taoyuan (TW); Hsin-Hsien Wu, Zhudong Township, Hsinchu County (TW)

(73) Assignee: Industrial Technology Research Institute, Chutung, Hsinchu (TW)

( * ) Notice: Subject to any disclaimer, the term of this patent is extended or adjusted under 35 U.S.C. 154(b) by 7 days.

(21) Appl. No.: 14/812,451

(22) Filed: Jul. 29, 2015

(65) Prior Publication Data

US 2016/0185802 A1 Jun. 30, 2016

(30) Foreign Application Priority Data

Dec. 26, 2014 (TW) .............................. 103145746 A

(51) Int. Cl.
*C07F 1/00* (2006.01)
*A01N 25/08* (2006.01)

(52) U.S. Cl.
CPC .................................. *A01N 25/08* (2013.01)

(58) Field of Classification Search
CPC ........................................................ C07F 1/005
USPC ..................................... 556/9, 116; 424/618
See application file for complete search history.

(56) References Cited

U.S. PATENT DOCUMENTS

| | | | |
|---|---|---|---|
| 4,608,247 A | 8/1986 | Heinig, Jr. | |
| 6,228,491 B1 | 5/2001 | Antelman | |
| 7,863,264 B2 | 1/2011 | Vange et al. | |
| 8,192,765 B2 | 6/2012 | Sarangapani | |
| 2005/0112339 A1* | 5/2005 | Sandel | A01N 43/40 428/206 |
| 2008/0269186 A1* | 10/2008 | Bignozzi | C07D 213/79 514/185 |
| 2011/0262556 A1 | 10/2011 | Holladay et al. | |
| 2012/0089068 A1 | 4/2012 | McClure, Jr. | |

FOREIGN PATENT DOCUMENTS

| | | |
|---|---|---|
| CN | 1886045 A | 12/2006 |
| CN | 102517888 | 6/2012 |
| CN | 102952954 | 3/2013 |
| CN | 103027078 | 4/2013 |
| CN | 203303250 | 11/2013 |
| CN | 103756487 | 4/2014 |
| CN | 103756488 | 4/2014 |
| KR | 20050009129 | 1/2005 |
| KR | 20090080161 | 7/2009 |
| TW | 201404722 A | 2/2014 |
| TW | 201424588 | 7/2014 |
| TW | I448300 | 8/2014 |

OTHER PUBLICATIONS

Office Action (Issuance Date: May 10, 2016) of corresponding TW Application No. 103145746, without English translation.
Gargiulo et al., "Silver-containing mesoporous bioactive glass with improved antibacterial properties", Journal of Materials Science Materials in Medicine, Sep. 2013, 23 pages.
Tian et al., "Facile, One-Pot Synthesis, and Antibacterial Activity of Mesoporous Silica Nanoparticles Decorated with Well-Dispersed Silver Nanoparticles", ACS Applied Materials & Interfaces, 2014, pp. 12038-12045, vol. 6.
Kumar et al., "Sorption Behavior of Thiourea-Grafted Polymeric Resin toward Silver Ion, Reduction to Silver Nanoparticles, and Their Antibacterial Properties", I&EC Research, 2013, pp. 6438-6445, vol. 52.
Zhu et al., "Preparation and antibacterial property of silver-containing mesoporous 58S bioactive glass", Materials Science and Engineering C, 2014, pp. 22-30.
Lin et al., "Evaluation of the Antibacterial Activity and Biocompatibility for Silver Nanoparticles Immobilized on Nano Silicate Platelets", ACS Applied Materials & Interfaces, 2013, pp. 433-443, vol. 5.

* cited by examiner

*Primary Examiner* — Porfirio Nazario Gonzalez
(74) *Attorney, Agent, or Firm* — Muncy, Geissler, Olds & Lowe, P.C.

(57) ABSTRACT

An antimicrobial composite material and a method for fabricating the same are provided. The antimicrobial composite material includes a porous material, a chelating agent, and a multivalent metal ion. The chelating agent is chemically bonded to the porous material, and the multivalent metal ion is chemically bonded to the chelating agent.

19 Claims, 3 Drawing Sheets

ANTIMICROBIAL COMPOSITE MATERIAL AND METHOD FOR FABRICATING THE SAME

CROSS REFERENCE TO RELATED APPLICATIONS

This application claims the benefit of Taiwan application Serial No. 103145746, filed Dec. 26, 2014, the subject matter of which is incorporated herein by reference.

TECHNICAL FIELD

The disclosure relates in general to an antimicrobial composite material and a method for fabricating the same.

BACKGROUND

Common antimicrobial material can be divided into three categories: natural antimicrobial materials, organic antimicrobial materials and inorganic antimicrobial materials. Inorganic antimicrobial material containing silver ion has been developed vigorously due to its wide effectiveness and safety. In comparison with using antibiotics or other organic compounds (e.g. sodium hypochlorite, etc.) using silver ion is more environmental friendly and less drug resistant. Developing an antimicrobial material with stability and long-lasting antibacterial effect is the trend of the times.

SUMMARY

One embodiment of the disclosure provides an antimicrobial composite material, comprising a porous material, a chelating agent chemically bonded to the porous material and a multivalent metal ion chemically bonded to the chelating agent.

One embodiment of the disclosure provides a method of manufacturing an antimicrobial composite material, comprising the following steps. Forming an oxidizing mixture, comprising: mixing an oxidizing agent and an ionic compound, wherein the ionic compound has a multivalent metal ion. Modifying a porous material with a chelating agent to form a modified porous material, wherein the chelating agent chemically bonds to the porous material. Mixing the oxidizing mixture and the modified porous material to form the antimicrobial composite material, wherein the multivalent metal ion chemically bonds to the chelating agent on the modified porous material.

DETAILED DESCRIPTION

Figure 1A:
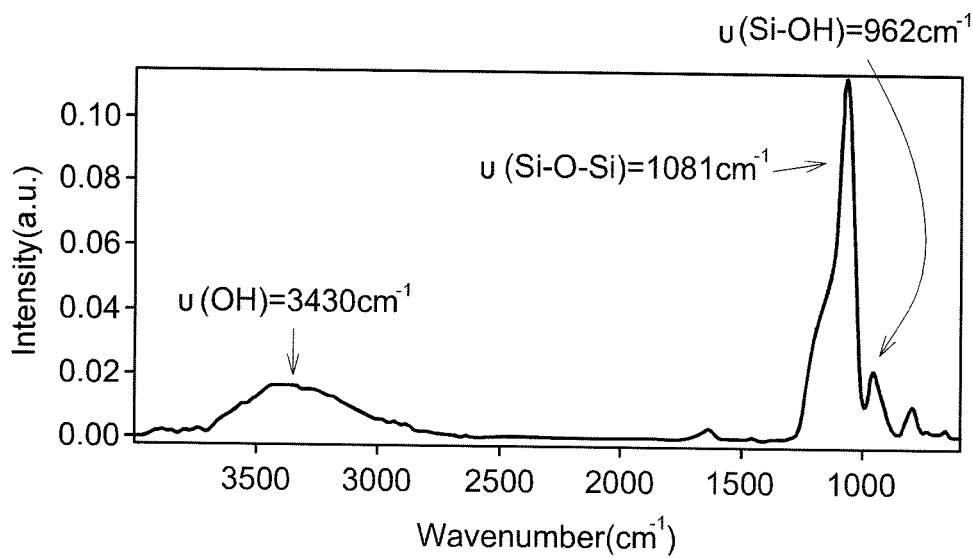
FIG. 1A is a spectrum of SBA-15 without $NH_2$ group measured by Fourier transform infrared spectroscopy (FTIR) according to one embodiment of the disclosure.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

The disclosure provides an antimicrobial composite material and a method for fabricating the same. According to some embodiments of the disclosure, a multivalent metal ion of the antimicrobial composite material can be stabilized and remain multivalent by using a chelating agent. The multivalent metal ion bonds to a porous material via the chelating agent. Therefore, high antibacterial ability and long-lasting antibacterial effect of the antimicrobial composite material can be achieved.

In some embodiments, an antimicrobial composite material, comprising a porous material, a chelating agent chemically bonded to the porous material and a multivalent metal ion chemically bonded to the chelating agent.

In comparison with the divalent metal ion bonding to a chelating agent in the embodiment, the divalent ionic compound is less stable in its valence number due to the effect of light and other environmental factors. Therefore, the divalent ionic compound has a shorter antibacterial effective time period.

In some embodiments, the high surface area of the porous material can increase the antibacterial ability of the divalent metal ion bonded to the porous material via the chelating agent.

In some embodiments, the chelating agent is chemically bonded to the porous material and the multivalent metal ion is chemically bonded to the chelating agent. In comparison with disposing the multivalent metal ion on the porous material via physical adsorption or hydrogen bonding, the structure of the antimicrobial composite material is more stable by chemical bonding the multivalent metal ion to the porous material via the chelating agent. The metal ion of the antimicrobial composite material does not easily dissolved in the environment and has a good solvent resistance that give rise to a long-lasting antibacterial effect.

In some embodiments, molar ratio of the multivalent metal ion to the chelating agent is about 0.5:1 to 20:1.

In some embodiments, the multivalent metal ion comprises divalent silver ion ($Ag^{2+}$), trivalent silver ion ($Ag^{3+}$), trivalent cobalt ion ($Co^{3+}$), trivalent nickel ion ($Ni^{3+}$) or a combination thereof.

In some embodiments, the molar ratio of the multivalent metal ion to the chelating agent is about 0.5:1 to 10:1 when the multivalent metal ion is divalent silver ion ($Ag^{2+}$), trivalent silver ion ($Ag^{3+}$) or a combination thereof.

In some embodiments, the molar ratio of the multivalent metal ion to the chelating agent is about 1:1 to 20:1 when the multivalent metal ion is trivalent cobalt ion ($Co^{3+}$), trivalent nickel ion ($Ni^{3+}$) or a combination thereof.

In some embodiments, the antimicrobial composite material comprises about 10 wt % to 50 wt % of the multivalent metal ion.

In some embodiments, the molar ratio of the porous material to a sum of the chelating agent and the multivalent metal ion is about 1:0.5 to 1:20. In other words, the molar ratio of the porous material to the chelating agent chemically bonded with the multivalent metal ion on its surface is about 1:0.5 to 1:20.

In some embodiments, the chelating agent comprises ethylene diamine tetra acetic acid (EDTA), nitrilotriacetic acid (NTA), 1-hydroxy ethylidene-1,1-diphosphonic acid (HEDP), ethylene diamine tetramethylene phosphonic acid sodium (EDTMPS), or a combination thereof.

In some embodiments, the porous material comprises a silicon-containing mesoporous material, an aluminum-containing mesoporous material, zeolite, activated carbon, or a combination thereof. In some embodiments, the porous material may comprise silicon oxide mesoporous material (e.g. silicon oxide mesoporous molecular sieves, SBA-15, with a pore size of about 2 nm to 50 nm).

According to some embodiments of the disclosure, a method for fabricating an antimicrobial composite material comprising the following steps. Mixing an oxidizing agent and an ionic compound to form an oxidizing mixture, wherein the ionic compound has a multivalent metal ion. In some embodiments, the oxidizing agent can be potassium persulfate, hydrogen peroxide, ozone, potassium permanganate, or a combination thereof. The ionic compound can be metal oxide, metal hydroxide, metal sulfide, metal halide or nitrate. In some embodiments, the multivalent metal ion comprises divalent silver ion ($Ag^{2+}$), trivalent silver ion ($Ag^{3+}$), trivalent cobalt ion ($Co^{3+}$), trivalent nickel ion ($Ni^{3+}$) or a combination thereof.

In some embodiments, after forming the oxidizing mixture, the pH value of the oxidizing mixture can be adjusted to about 4 to 8 by adding acidic solution or basic solution. Then heating the oxidizing mixture at 60° C. to 120° C. for about 2 hours to 6 hours.

Modifying a porous material with a chelating agent to form a modified porous material, wherein the chelating agent chemically bonds to the porous material. In some embodiments, before modifying the porous material with the chelating agent to form the modified porous material, the method further comprises functionalizing the porous material to form a functional group on the porous material. The chelating agent can chemically bonds to the porous material via the functional group. The functional group can be but not limited to —$NH_2$, —SH or —$SO_3H$.

In some embodiments, the porous material comprises a silicon-containing mesoporous material, an aluminum-containing mesoporous material, zeolite, activated carbon, or a combination thereof.

In some embodiments, the chelating agent comprises ethylene diamine tetra acetic acid (EDTA), nitrilotriacetic acid (NTA), 1-hydroxy ethylidene-1,1-diphosphonic acid (HEDP), ethylene diamine tetramethylene phosphonic acid sodium (EDTMPS), or a combination thereof.

Mixing the oxidizing mixture and the modified porous material to form the antimicrobial composite material, wherein the multivalent metal ion chemically bonds to the chelating agent on the modified porous material.

In some embodiments, the molar ratio of the porous material to a sum of the chelating agent and the multivalent metal ion is about 1:0.5 to 1:20.

In some embodiments, after mixing the oxidizing mixture and the modified porous material, the method further comprises filtering, washing and drying the mixture of the oxidizing mixture and the modified porous material to get the antimicrobial composite material. And the multivalent metal ion chemically bonds to the chelating agent on the modified porous material.

In some embodiments, the antibacterial ability of the antimicrobial composite material made by aforementioned method was measured with disc diffusion test and dilution susceptibility test.

The zone of inhibition (antibacterial circle radius) of the antimicrobial composite material of the embodiments measured with disc diffusion test is bigger than that of silver nanoparticles and that of the antimicrobial composite material without porous structure.

The multivalent metal ion in the disclosure means the metal ion having a valence number of more than 2.

EXAMPLES

Example 1: Fabricating the Antimicrobial Composite Material Containing Silver Ion Comprises the Following Three Steps Step 1: fabricating the mesoporous material (e.g. silicon oxide mesoporous molecular sieves, SBA-15, with a pore size of about 8 nm to 9 nm).

Step 2: SBA-15 and surfactant were mixed in a reaction bottle. Aminopropyltriethoxysilane (APTES) was added into the reaction bottle in an acidic environment. And the mixture in the bottle was heated at 40° C. for 20 hours, and then was heated at 100° C. for 20 hours. The reaction result was stood to room temperature and dried naturally for 20 hours, and then a dried product was formed. The dried product was washed with ethanol to remove the surfactant, and then a functional group (—$NH_2$) was formed on SBA-15 ($NH_2$-SBA-15).

Figure 1B:
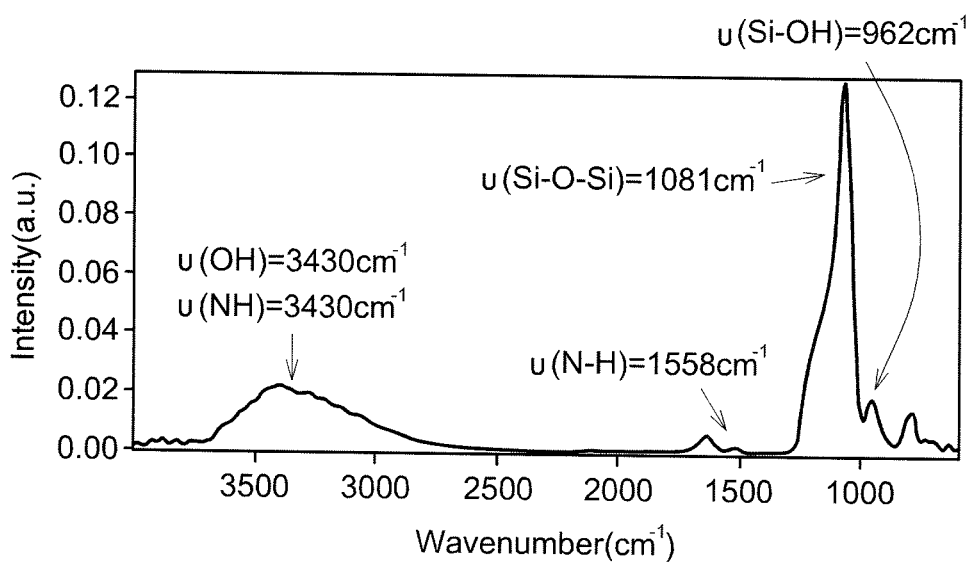
FIG. 1B is a spectrum of SBA-15 with $NH_2$ group measured by Fourier transform infrared spectroscopy (FTIR) according to one embodiment of the disclosure.

FIG. 1A is a spectrum of SBA-15 (the product of step 1) measured by Fourier transform infrared spectroscopy (FTIR). FIG. 1B is a spectrum of $NH_2$-SBA-15 (the product of step 2) measured by Fourier transform infrared spectroscopy (FTIR). The peak at 3430 $nm^{-1}$ represents OH group in SBA-15. The peak with wavelength 1080 $nm^{-1}$ features Si—O—Si in zeolite. The peak at 1558 $nm^{-1}$ in FIG. 1B represents amino group in zeolite. That means amino group ($NH_2$) was bonded to SBA-15.

Step 3: $NH_2$-SBA-15 (the product of step 2), EDTA and water were mixed and stirred at room temperature for 2 hours to form a mixture. The mixture was filtered and a solid product was formed. Using deionized water to wash the solid product. Then SBA-15 bonded with EDTA (EDTA-SBA-15) was obtained.

Step 4: Potassium persulfate, silver nitrate and water were mixed to form a mixture. Adjusted the pH value of the mixture to about 4 to 8 by adding acidic solution or basic solution. Then the mixture was heated at 85° C.

Step 5: EDTA-SBA-15 (the product of step 3) was mixed with the mixture (the product of step 4) and proceeded to a dehydrogenation reaction. The antimicrobial composite material bonded to divalent silver ion was obtained.

Figure 2:
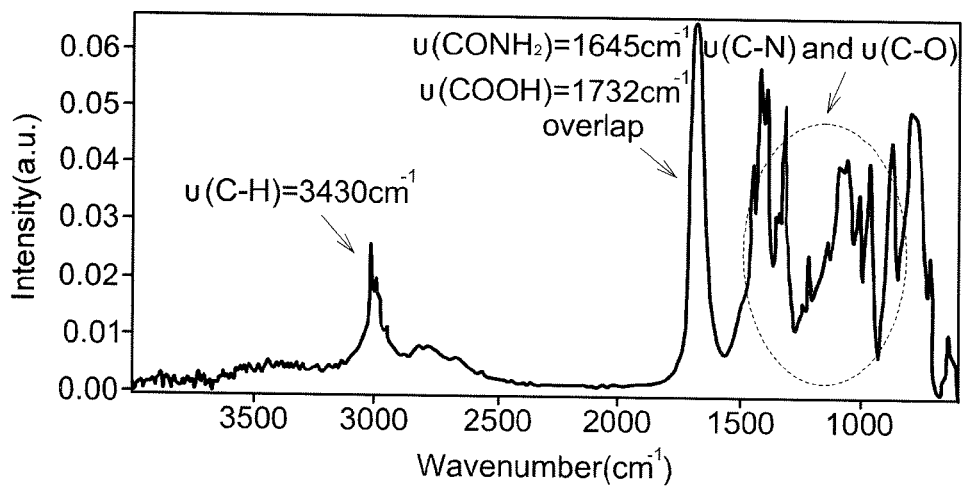
FIG. 2 is a spectrum of SBA-15 with ethylenediaminetetraacetic acid (EDTA) measured by Fourier transform infrared spectroscopy (FTIR) according to one embodiment of the disclosure.

FIG. 2 is a spectrum of EDTA-SBA-15 (the product of step 3) measured by Fourier transform infrared spectroscopy (FTIR). The peak at 3000 $nm^{-1}$ represents CH group in EDTA-SBA-15. The peak at 3000 $nm^{-1}$ represents CH group in EDTA-SBA-15. The peak at 1645 $nm^{-1}$ represents $CONH_2$ group in EDTA-SBA-15. The peak at 1732 $nm^{-1}$ represents COOH group in EDTA-SBA-15. The peak at 1300 cm$^{-1}$~1000 cm$^{-1}$ represents CN group and CO group in EDTA-SBA-15. That means EDTA was bonded to SBA-15.

Figure 3:
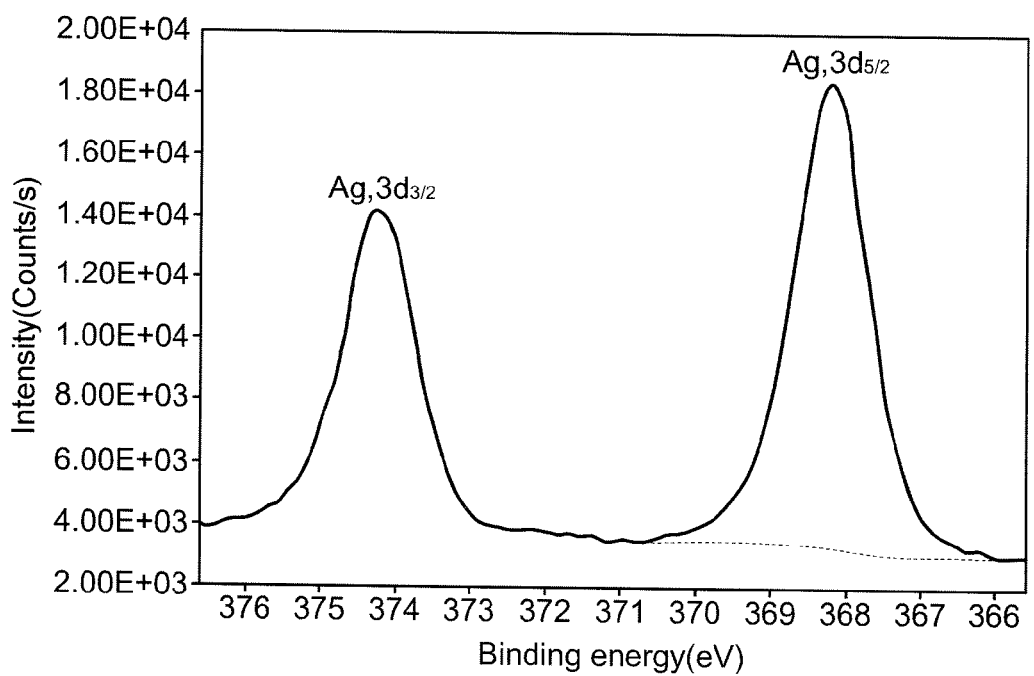
FIG. 3 is a spectrum of an antimicrobial composite material chemically bonded with divalent silver ion measured by X-ray photoelectron spectroscopy (XPS) according to one embodiment of the disclosure.

FIG. 3 is a spectrum of an antimicrobial composite material chemically bonded with divalent silver ion (the product of step 5) measured by X-ray photoelectron spectroscopy (XPS). The shape and binding energy of the peak in XPS spectrum represent the existence of divalent silver ion. And the change in valence number of the silver ion was occurred when the silver ion was boned to EDTA. That means EDTA was bonded to SBA-15. According to the areal integral of $Ag_{3d5}$ peak, the atomic ratio of nonvalent silver ion:monovalent silver ion:divalent silver ion is 17.1:71.6:11.3.

Comparison Example 1

Using silver nanoparticles as the antimicrobial composite material.

Comparison Example 2

Using SBA-15 as the antimicrobial composite material.

Comparison Example 3

Using Gentamicin as the antimicrobial composite material.

Comparison Example 4

Using Ampicillin as the antimicrobial composite material.

Comparison Example 5-6

8 g Potassium persulfate, 0.5M silver nitrate and water were mixed to form a mixture. Adjusted the pH value of the mixture to about 4 to 8 by adding acidic solution or basic solution. Then the mixture was heated at 85° C. Then EDTA was instilled into the mixture, and stirred. The reaction result was stood to room temperature and was filtered to obtain a solid product and a solution product. The solution product is the product of comparison Example 5. The solid product is the product of comparison experiment 6.

The antibacterial ability of the antimicrobial composite material made by aforementioned method was measured with disc diffusion test In some embodiments, the antibacterial ability of the antimicrobial composite material made by aforementioned method was measured and shows in table 1 and FIG. 2-3. The product of comparison Example 5 is a multivalent silver ion liquid suspension. The product of comparison Example 6 is a solid product of a multivalent silver ion. The product of Example 1 is a solid product of a multivalent silver ion bonded to a mesoporous material.

[Disc Diffusion Test]

The antibacterial ability of the antimicrobial composite material of Example 1 and comparison Example 1-6 was measured with disc diffusion test. A bacterial suspension having an inoculum density of approximately 1.5×10$^8$ CFU/ml was added to agar and poured into a plastic Petri dish. After hardening of the agar, filter paper discs (φ6 mm) had been impregnated with the antimicrobial composite material were placed on the agar. In each test, after an incubation period of 18-20 hours at 37° C., a clear zone of inhibition was evident around discs that contained antimicrobial composite material. The concentration of the antimicrobial composite materials was shown in Table 1. The bigger the antibacterial circle radius is, the stronger antibacterial effect is.

TABLE 1

| antimicrobial composite material | concentration of sample (μg) | zone of inhibition (antibacterial circle radius) (mm) | |
|---|---|---|---|
| | | E. coli | S. aureus |
| product of Example 1 | 95 | 20.2 | 21.3 |
| product of Comparison Example 1 | 500 | 6.5 | 7.5 |
| product of Comparison Example 2 | 500 | — | — |
| Comparison Example 3 (Gentamicin) | 10 | 19.7 | 20.3 |
| Comparison Example 4 (Ampicillin) | 10 | 16.5 | 31.3 |
| product of Comparison Example 5 (silver ion liquid suspension) | 0.2 | 13.7 | 16.0 |
| product of Comparison Example 6 (a solid product of a multivalent silver ion) | 250 | 22.2 | 22.2 |

—: zone of inhibition was not shown

According to the results of Table 1, Example 1 has almost the same antibacterial effect as Gentamicin and Ampicillin in an amount of 95 μg. The product of Example 1, a multivalent silver ion bonded to a mesoporous material, has almost the same antibacterial effect as Comparison Example 6 in an amount of 95 μg much smaller than the amount of the product of Comparison Example 6. Bonding a multivalent silver ion to a mesoporous material does not decrease the antibacterial effect, and can be even more antibacterial effective than a multivalent silver ion without a mesoporous material in the same usage amount.

According to the results of Table 1, the antibacterial circle radius of Ampicillin to S. aureus is 31.3 mm and the antibacterial circle radius of Gentamicin to S. aureus is 16.5 mm. There is no inhibition zone around the disc of filter paper when SBA-15 was used alone. It means that the results of Table 1 are reliable.

[Dilution Susceptibility Test]

The minimum amount of antimicrobial composite material for the inhibition of S. aureus or E. coli was determined by Dilution Susceptibility Test. Antibacterial ability of the antimicrobial composite materials of Example 1 and comparison Example 1-6 can be estimated according to the minimum inhibition amount of antimicrobial composite material of S. aureus or E. coli. Plating a range of bacterial suspension on a sterile 96 well plate containing a range of antimicrobial composite material concentrations (as shown in Table 2). After an incubation period of 16 hours at a constant temperature, measured bacterial OD600 to get bacterial concentration by Microplate Absorbance Reader and calculated the minimum amount of antimicrobial composite material for the inhibition of bacteria. The results in Table 2 shows an estimate of the concentration that inhibits 50% ($MIC_{50}$), 90% ($MIC_{90}$) and 99% ($MIC_{99}$) of bacterial and can indicate shifts in the susceptibility of bacterial antimicrobial composite material, and shows an estimate of the concentration of the multivalent silver ion (the minimum amount of the multivalent silver ion for the inhibition of bacteria).

TABLE 2

| antimicrobial composite material | E. coli (100 μL, 1.5 × 10⁸ CFU/mL) | | | S. aureus (50 μL, 1.5 × 10⁸ CFU/mL) | | |
|---|---|---|---|---|---|---|
| | $MIC_{50}$ | $MIC_{90}$ | $MIC_{99}$ | $MIC_{50}$ | $MIC_{90}$ | $MIC_{99}$ |
| product of Example 1 | 0.3 | 0.4 | 0.4 | 0.3 | 0.4 | 0.7 |

Comparison Example 7-10

According to Table 3, different forms of silica were provided. Different silver materials deposited on different forms of silica in different ways (as shown in Table 3). The measuring results for each example were shown in Table 3.

TABLE 3

| antimicrobial composite material | different forms of silica | different silver materials deposited on different forms of silica in different ways | minimum amount of antimicrobial composite material for the inhibition of bacteria (μg/mL, $MIC_{99}$) | |
|---|---|---|---|---|
| | | | E. coli | S. aureus |
| product of Example 1 | SBA-15 | multivalent silver ion chemically bonded to the surface and pores of SBA-15 | 42 | 77 |
| Comparison Example 7 | silica nanoparticle | silver nanoparticles adsorbed on the silica nanoparticle | 2000 | 2000 |
| Comparison Example 8 | silica nanofiber | silver nanoparticles adsorbed on the silica nanofiber | 1000 | — |
| Comparison Example 9 | silica nanoparticle | silver nanoparticles adsorbed on the silica nanoparticle | 100 | — |
| Comparison Example 10 | SBA-15 | silver nanoparticles adsorbed on the surface and pores of SBA-15 | 80 | 320 |

—: the test did not perform

Comparison Example 7: J. Phys. Chem. C 2007, 111, 3629-3635
Comparison Example 8: Colloids and Surfaces A: Physicochem. Eng. Aspects 387 (2011) 57-64
Comparison Example 9: Adv. Mater. 2009, 21, 1684-1689
Comparison Example 10: ACS Appl. Mater. Interfaces 2014, 6, 12038-12045

According to Table 2, $MIC_{99}$ of E. coli of both Example 1 and Comparison Example 6 are 0.4 μg. $MIC_{99}$ of S. aureus of Example 1 and Comparison Example 6 are 0.5 μg and 0.7 μg.

According to Table 3, $MIC_{99}$ of E. coli and S. aureus of Example 1 were less than that of Comparison Example 7-10. In comparison with disposing the multivalent metal ion on the porous material via physical adsorption, the structure of the antimicrobial composite material is more stable by chemical bonding the multivalent metal ion to the porous material via the chelating agent.

[Ratio of Decade]

Figure 4:
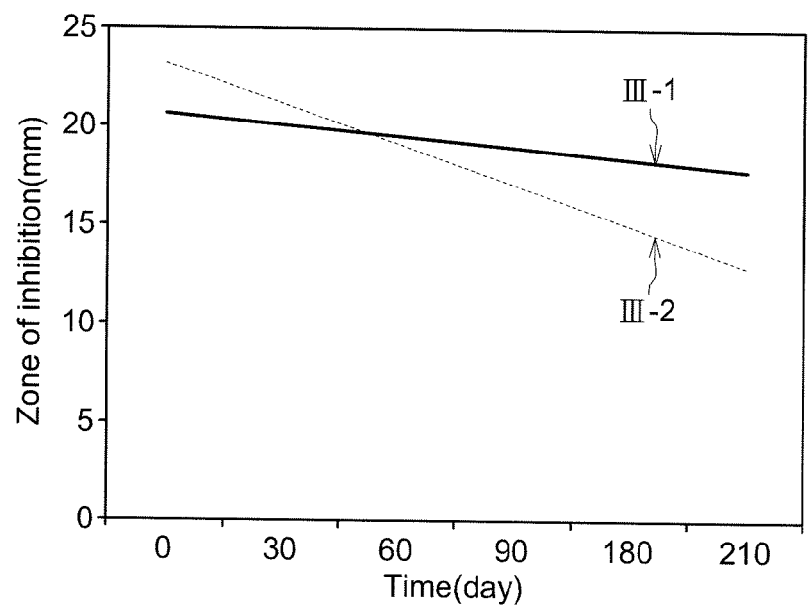
FIG. 4 shows the relationship between time and zone of inhibition (antibacterial circle radius) of E. coli according to one embodiment and one comparison experiment of the disclosure.
Figure 5:
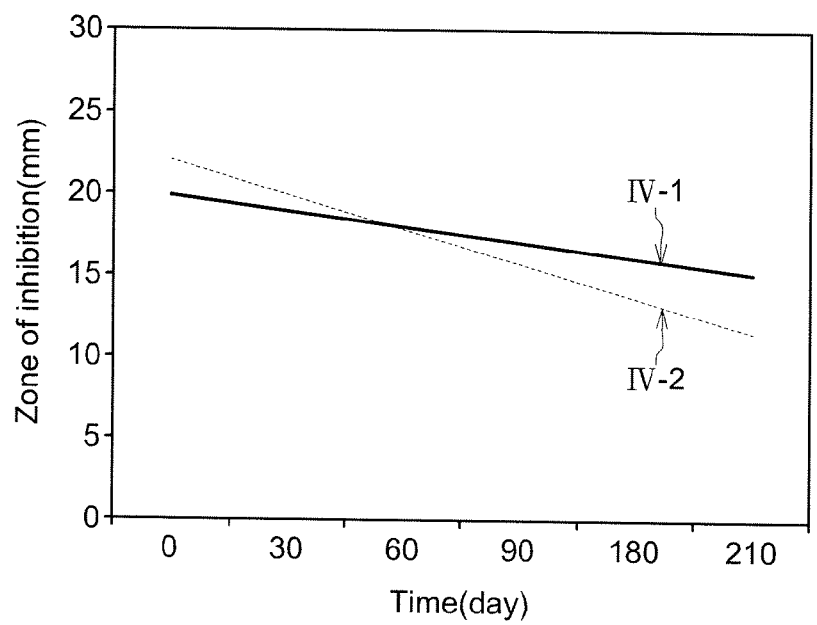
FIG. 5 shows the relationship between time and zone of inhibition (antibacterial circle radius) of S. aureus according to one embodiment and one comparison experiment of the disclosure.

FIG. 4 shows the relationship between time and zone of inhibition of E. coli according to Example 1 (III-1) and Comparison Example 6 (III-2). FIG. 5 shows the relationship between time and zone of inhibition of S. aureus according to Example 1 (IV-1) and Comparison Example 6 (IV-2).

The ratio of decade of Example 1 and Comparison Example 6 were measured by Disc Diffusion Test in a range of time (0-210 days). According to FIG. 4-5, the antimicrobial composite material of Example 1 has a better long-lasting antibacterial effect than Comparison Example 6. The antibacterial effect against S. aureus and E. coli of the antimicrobial composite material of Example 1 maintained at about 60% after 210 days. The antibacterial effect against S. aureus and E. coli of the antimicrobial composite material of Comparison Example 6 maintained at about 40% after 210 days. The antimicrobial composite material of the embodiment of the disclosure has a better long-lasting antibacterial effect than a multivalent silver ion without chemically bonding to a mesoporous material.

It will be apparent to those skilled in the art that various modifications and variations can be made to the disclosed methods and materials. It is intended that the specification and Examples be considered as exemplary only, with a true scope of the disclosure being indicated by the following claims and their equivalents.

What is claimed is:

1. An antimicrobial composite material, comprising:
   a porous material;
   a chelating agent chemically bonded to the porous material; and
   a multivalent metal ion chemically bonded to the chelating agent, the antimicrobial composite material comprises 10 wt % to 50 wt % of the multivalent metal ion.

2. The antimicrobial composite material as claimed in claim 1, wherein a molar ratio of the multivalent metal ion to the chelating agent is 0.5:1 to 20:1.

3. The antimicrobial composite material as claimed in claim 1, wherein the multivalent metal ion comprises divalent silver ion ($Ag^{2+}$), trivalent silver ion ($Ag^{3+}$), trivalent cobalt ion ($Co^{3+}$), trivalent nickel ion ($Ni^{3+}$) or a combination thereof.

4. The antimicrobial composite material as claimed in claim 3, wherein a molar ratio of the multivalent metal ion to the chelating agent is 0.5:1 to 10:1 when the multivalent metal ion is divalent silver ion ($Ag^{2+}$), trivalent silver ion ($Ag^{3+}$) or a combination thereof.

5. The antimicrobial composite material as claimed in claim 3, wherein a molar ratio of the multivalent metal ion to the chelating agent is 1:1 to 20:1 when the multivalent metal ion is trivalent cobalt ion ($Co^{3+}$), trivalent nickel ion ($Ni^{3+}$) or a combination thereof.

6. The antimicrobial composite material as claimed in claim 1, wherein a molar ratio of the porous material to a sum of the chelating agent and the multivalent metal ion is 1:0.5 to 1:20.

7. The antimicrobial composite material as claimed in claim 1, wherein the chelating agent comprises ethylene diamine tetra acetic acid (EDTA), nitrilotriacetic acid (NTA), 1-hydroxy ethylidene-1,1-diphosphonic acid (HEDP), ethylene diamine tetramethylene phosphonic acid sodium (EDTMPS), or a combination thereof.

8. The antimicrobial composite material as claimed in claim 1, wherein the porous material comprises a silicon-containing mesoporous material, an aluminum-containing mesoporous material or a combination thereof.

9. The antimicrobial composite material as claimed in claim 1, wherein the porous material comprises zeolite, activated carbon, or a combination thereof.

10. A method of manufacturing an antimicrobial composite material, comprising the following steps:
    forming an oxidizing mixture, comprising:
    mixing an oxidizing agent and an ionic compound, wherein the ionic compound has a multivalent metal ion;
    modifying a porous material with a chelating agent to form a modified porous material, wherein the chelating agent chemically bonds to the porous material; and
    mixing the oxidizing mixture and the modified porous material to form the antimicrobial composite material, wherein the multivalent metal ion chemically bonds to the chelating agent on the modified porous material.

11. The method of manufacturing the antimicrobial composite material as claimed in claim 10, wherein forming the oxidizing mixture further comprises:
    adjusting a pH value of the oxidizing mixture to 4 to 8 by adding acidic solution or basic solution; and
    heating the oxidizing mixture.

12. The method of manufacturing the antimicrobial composite material as claimed in claim 10, wherein the oxidizing agent comprises potassium persulfate, hydrogen peroxide, ozone, potassium permanganate, or a combination thereof.

13. The method of manufacturing the antimicrobial composite material as claimed in claim 11, wherein the oxidizing mixture is heated at 60° C. to 120° C. for 2 hours to 6 hours.

14. The method of manufacturing the antimicrobial composite material as claimed in claim 10, wherein before modifying the porous material with the chelating agent to form the modified porous material, the method further comprises:
    functionalizing the porous material to form a functional group on the porous material, and
    the chelating agent chemically bonds to the porous material via the functional group.

15. The method of manufacturing the antimicrobial composite material as claimed in claim 10, wherein the multivalent metal ion comprises divalent silver ion ($Ag^{2+}$), trivalent silver ion ($Ag^{3+}$), trivalent cobalt ion ($Co^{3+}$), trivalent nickel ion ($Ni^{3+}$) or a combination thereof.

16. The method of manufacturing the antimicrobial composite material as claimed in claim 10, wherein the chelating agent comprises ethylene diamine tetra acetic acid (EDTA), nitrilotriacetic acid (NTA), 1-hydroxy ethylidene-1,1-diphosphonic acid (HEDP), ethylene diamine tetramethylene phosphonic acid sodium (EDTMPS), or a combination thereof.

17. The method of manufacturing the antimicrobial composite material as claimed in claim 10, wherein a molar ratio of the porous material to a sum of the chelating agent and the multivalent metal ion is 1:0.5 to 1:20.

18. The method of manufacturing the antimicrobial composite material as claimed in claim 10, wherein the porous material comprises a silicon-containing mesoporous material, an aluminum-containing mesoporous material or a combination thereof.

19. The method of manufacturing the antimicrobial composite material as claimed in claim 10, wherein the porous material comprises zeolite, activated carbon, or a combination thereof.

* * * * *